United States Patent
Wollschläger

(10) Patent No.: US 7,611,497 B2
(45) Date of Patent: Nov. 3, 2009

(54) DEVICE FOR HANDLING A CATHETER

(76) Inventor: Helmut Wollschläger, Gabrielistrasse 9, 90480 Nürnberg (DE)

(*) Notice: Subject to any disclaimer, the term of this patent is extended or adjusted under 35 U.S.C. 154(b) by 243 days.

(21) Appl. No.: 11/483,323

(22) Filed: Jul. 7, 2006

(65) Prior Publication Data
US 2007/0045504 A1    Mar. 1, 2007

Related U.S. Application Data

(63) Continuation of application No. PCT/EP2004/013701, filed on Dec. 2, 2004.

(30) Foreign Application Priority Data
Jan. 8, 2004    (DE) ................. 10 2004 001 461

(51) Int. Cl.
*A61M 5/00* (2006.01)
*A61M 1/00* (2006.01)
*F16K 7/04* (2006.01)

(52) U.S. Cl. ............... 604/246; 251/4; 251/7; 604/30

(58) Field of Classification Search .......... 604/30, 604/33, 34, 174, 175, 178, 243, 246, 249, 604/250, 256; 251/4, 7
See application file for complete search history.

(56) References Cited

U.S. PATENT DOCUMENTS

| | | | | |
|---|---|---|---|---|
| 1,106,518 A | * | 8/1914 | Matti | 81/319 |
| 1,108,737 A | * | 8/1914 | Gajdos | 606/147 |
| 1,110,220 A | * | 9/1914 | Millsap | 81/316 |
| 4,538,485 A | * | 9/1985 | Saila | 81/336 |
| 5,338,313 A | * | 8/1994 | Mollenauer et al. | 604/249 |
| 5,887,486 A | * | 3/1999 | Lin et al. | 74/489 |
| 5,921,968 A | * | 7/1999 | Lampropoulos et al. | 604/246 |

(Continued)

FOREIGN PATENT DOCUMENTS

DE    195 26 075 C1    12/1996

(Continued)

*Primary Examiner*—Kevin C Sirmons
*Assistant Examiner*—William Carpenter
(74) *Attorney, Agent, or Firm*—Harness, Dickey & Pierce, P.L.C.

(57) ABSTRACT

The invention relates to a device for handling a catheter with an elongate valve body (12), a lever arm (26) which is, pre-stressed by means of a spring element and mounted pivotably on the valve body (12) so as to be pivotable from a first end position into a second end position (34) counter to the pre-stressing force of the spring element, a pressure piston (24) which is received in the valve body (12) and can be moved in the longitudinal direction by means of the lever arm (26) in order to open a sealing element in the valve body (12) when the lever arm (26) is moved in the direction of the second end position (34), and a catch mechanism (40) which has an arresting arrangement (42) and a catch tongue (50) interacting therewith in order to hold the lever arm (26) in at least one catching position. The catch mechanism (40) is designed in such a way that the arresting arrangement (42) and the catch tongue (50) come out of engagement when the second end position (34) of the lever arm (26) is reached, so that the spring element guides the lever arm (26) back into the first end position (FIG. 1).

7 Claims, 2 Drawing Sheets

U.S. PATENT DOCUMENTS

| | | | |
|---|---|---|---|
| 5,941,499 A * | 8/1999 | Wollschlager | 251/4 |
| 5,968,052 A | 10/1999 | Sullivan, III et al. | |
| 6,572,590 B1 * | 6/2003 | Stevens et al. | 604/246 |
| 6,695,818 B2 * | 2/2004 | Wollschlager | 604/174 |
| 6,986,749 B2 * | 1/2006 | Wollschlager | 600/585 |

FOREIGN PATENT DOCUMENTS

| | | |
|---|---|---|
| DE | 199 48 409 C1 | 4/2001 |
| WO | WO 01/15768 A1 | 3/2001 |

* cited by examiner

DEVICE FOR HANDLING A CATHETER

CROSSREFERENCES TO RELATED APPLICATIONS

This application is a continuation of copending international patent application PCT/EP2004/013701, filed on Dec. 2, 2004 and designating the U.S., which claims priority of German patent application DE 10 2004 001 461.2, filed on Jan. 8, 2004.

BACKGROUND OF THE INVENTION

1. Field of the Invention

The invention relates to a device for handling a catheter with an elongate valve body, a lever arm which is prestressed by means of a spring element and mounted pivotably on the valve body so as to be pivotable from a first end position into a second end position counter to the prestressing force of the spring element, a pressure piston which is received in the valve body and can be moved in the longitudinal direction by means of the lever arm in order to open a sealing element in the valve body when the lever arm is moved in the direction of the second end position, and a catch mechanism which has an arresting arrangement and a catch tongue interacting therewith in order to hold the lever arm in at least one catching position.

2. Related Prior Art

Such a device is known from DE 195 26 075 C1, for example. In this device, for actuating a pressure piston introduced in a valve body by means of a lever arm, a flexible arresting piece with a catch nose is designed in one piece on a valve body, with which piece a catching end of the lever arm can be held in a catching position. The arresting piece extends essentially at right angles to the valve body. In the catching position, a clamping force is exerted on a catheter guided through the valve body and the pressure piston in order to secure the catheter against unintentional displacement in the axial direction.

A further such device is known from WO 01/15768 A1, for example. In this device, the arresting piece has a number of catch noses for locking the lever arm in a number of catching positions and an actuating wing which is aligned in prolongation of the lever arm in the catching positions of the lever arm.

SUMMARY OF THE INVENTION

Although the abovementioned device can be operated very easily and ergonomically, a desire exists on the part of the user for the usability to be improved further.

Against this background, the object of the present invention is to develop the device referred to in the introduction in such a way that easier operation is made possible.

This object is achieved in the abovementioned device by virtue of the fact that the catch mechanism is designed in such a way that the arresting arrangement and the catch tongue come out of engagement when the second end position of the lever arm is reached, so that the spring element guides the lever arm back into the first end position.

In other words, the catch mechanism is designed in such a way that the user simply has to press the lever arm into the second end position in order to arrive at the first end position again. When the lever arm reaches the second end position, the catch tongue is released from the arresting arrangement and as it were frees the catch mechanism, so that the lever arm can then move into the first end position. In this connection, the spring element ensures the return of the lever arm into the first end position.

The reason operation is so simple for the user is that in the end he has to perform only one movement of the lever arm, namely pressing the lever arm in the direction of the second end position. It is consequently no longer necessary to release the catching position of the lever arm by, for example, pressing an actuating wing as is proposed in the publication WO 01/15768 A1 referred to above.

In a preferred development of the invention, the arresting arrangement has a number of catch noses which are arranged along a concentric line around the fulcrum of the lever arm in order to define a number of catching positions of the lever arm between the two end positions.

These measures have the advantage that the several catching positions further simplify usability as the user can better adjust the clamping force acting on the catheter.

In a further preferred embodiment, the catch nose facing the valve body follows a guide surface extending at an angle in order, when the second end position of the lever arm is reached, to guide the catch tongue onto that side of the arresting arrangement facing away from the catch nose, so that the catch tongue cannot enter into engagement with the catch noses when the lever arm is returned into the first end position.

In other words, a surface which extends upward at an angle (away from the valve body) toward the rear surface in relation to the catch noses is provided at that end of the arresting arrangement facing the valve body. The catch tongue on the lever arm is thus guided onto the rear side of the catch noses when the second end position is reached, so that the catch tongue cannot come into contact with the catch noses during the travel of the lever arm into the first end position.

This measure results in a very simple design of the arresting arrangement and makes very safe operation possible.

In a further preferred embodiment, the catch tongue and the catch noses extend transversely to the longitudinal direction of the valve body.

This measure is especially simple as far as construction is concerned.

In a preferred development, the lever arm has an elongated hole, through which a lateral tube starting from the valve body extends.

This measure makes a very compact device with great stability possible, in particular also with regard to the lever arm, which can be stabilized additionally by the interaction of elongated hole and lateral tube.

The valve body and/or the lever arm are preferably designed as injection-molded parts, the valve body and the arresting arrangement preferably being provided as one-piece components.

Further advantages and developments of the invention emerge from the description and the accompanying drawing.

It is clear that the features mentioned above and those still to be explained below can be used not only in the combination indicated in each case but also in other combinations or individually without leaving the scope of the present invention.

BRIEF DESCRIPTION OF THE FIGURES

The invention is now explained by way of example with reference to a preferred embodiment and the drawing, in which.

DESCRIPTION OF PREFERRED EMBODIMENTS

Figure 1:
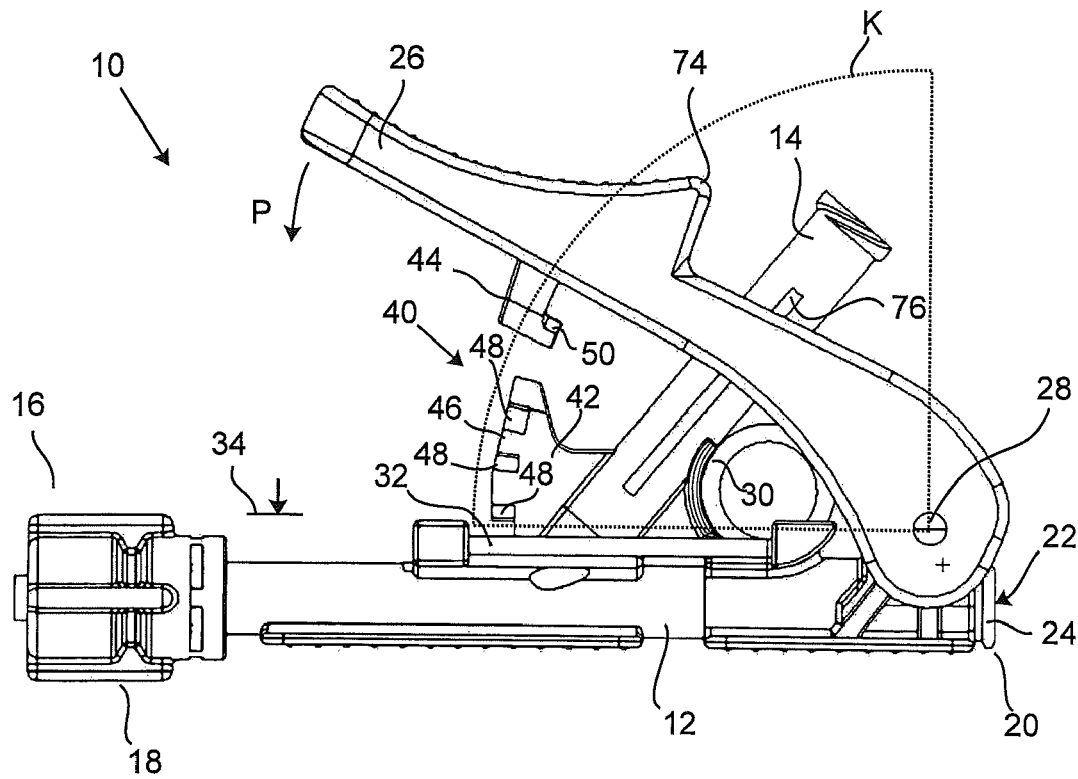
FIG. 1 shows a diagrammatic side view of the device according to the invention.

In FIG. 1, a device according to the invention is shown in a diagrammatic illustration from the side and designated by reference number 10. The device 10 has an elongate valve body 12 which has an axial valve body guide-through (not illustrated). The valve body 12 thus constitutes a tubular element which is open at both its ends. A lateral tube 14 is attached in one piece to the valve body 12 in a central longitudinal region, the lateral tube 14 extending at an angle to the longitudinal axis of the valve body, for example at an angle of 45°. In this connection, the lateral tube 14 runs into the valve body guide-through.

At a connection end 16, which faces away from the body of a patient when the device 10 is used as intended, a rotary cuff 18 is provided, with which the valve body 12 can be closed in a sealed way in a manner known per se when a guide catheter has been introduced. In an end 20 opposite the connection end 16, which faces the body of a patient when the device 10 is used as intended, a sealing arrangement 22 is provided, which consists of a pressure piston 24 and a sealing stopper provided in the valve body guide-through and located at the inner end of the pressure piston 24. The sealing stopper, which cannot be seen in FIG. 1, is made from an elastic material and has a continuous opening in the longitudinal direction which can be closed under pressure load in the longitudinal direction. This pressure load is applied to the sealing stopper by means of the pressure piston 24.

The device 10 also has a lever arm 26 which is mounted pivotably about a spindle 28 on the connection end 20.

The lever arm 26 is prestressed into a first end position shown in FIG. 1 by means of a torsion spring 30. For this, the torsion spring 30 provided with helical turns has an end portion 32 which is fixed to the valve body 12 and an end portion which is fixed to a surface of the lever arm 26 which faces the valve body 12 but cannot be seen in the figure.

The lever arm 26 can be rotated about the spindle 28 from the first end position, which is shown, in the direction of the arrow P into a second end position 34 counter to the force of the torsion spring 30. Without corresponding loading of the lever arm 26, it is guided back into the first end position, which is shown, again by means of the torsion spring 30.

A component not illustrated in FIG. 1, which interacts with the pressure piston 24 in such a way that, when the lever arm 26 is moved into the second end position 34, the pressure piston 24 is displaced in the longitudinal direction in order to reduce the load on the sealing stopper and thus to open the guide-through in the sealing stopper, is provided on the lever arm 26. In other words, the pressure piston 24 is pressed so strongly against the sealing stopper when the prestressed lever arm 26 is in the first end position that the guide-through is completely closed.

The purpose of such a medical device is generally known and is therefore not to be described in greater detail. Briefly, the device 10 serves for clamping sealingly by means of the sealing stopper a catheter running through the valve body 12; the clamping force can be reduced, in order for it to be possible to move the catheter in the longitudinal direction, by actuating the lever arm 26.

As for the rest, reference is made to WO 01/15768 with regard to the functioning and the construction of the valve body 12. The content of the disclosure of this publication is to this extent included in the present application by reference.

In order for it to be possible to hold the lever arm 26 in different positions, a catch mechanism 40 is provided, which comprises an arresting arrangement 42 assigned to the valve body 12 and a catch tongue arrangement 44 assigned to the lever arm 26.

The arresting arrangement 42 is designed as a plate-shaped part which is provided on the lateral tube 14. A number of catch noses 48, three by way of example in the present embodiment, are provided in the edge region 46 facing away from the lateral tube 14.

For its part, the catch tongue arrangement 44 has a catch tongue 50 which can interact with the catch noses 48. The catch noses 48 and the catch tongue 50 consequently lie on a concentric line K around the spindle 28.

The catch tongue arrangement 44 is provided on the lower side of the lever arm 26 facing the valve body, likewise in the form of a strip-shaped or plate-shaped element.

Figure 2:
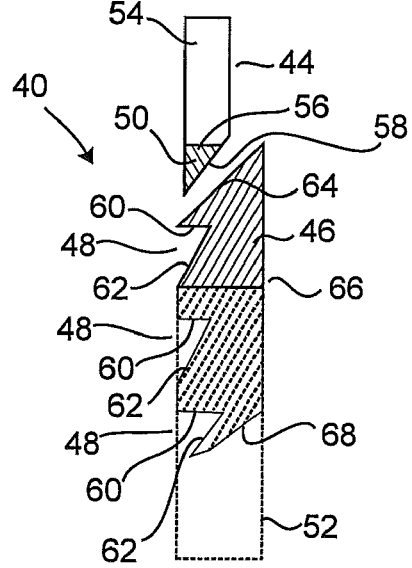
FIG. 2 shows a diagrammatic illustration of the catch mechanism.

The catch mechanism 40 is shown again, separately, in an enlarged diagrammatic illustration in FIG. 2. In this connection, the view is from the connection end 20, so that the plate-shaped part of the arresting arrangement 42, which is designated by reference number 52, conceals a portion of the edge region. This is illustrated by the dotted line and the slightly lighter hatching of the edge region 46.

The catch tongue 50 of the catch tongue arrangement 44 is designed as a triangular component, for example, which projects in relation to the basic body 54 of the catch tongue arrangement 44. With respect to the drawing plane in FIG. 2, the catch tongue 50 thus lies in front of the basic body 54. The catch tongue 50 has a catching surface 56 and a surface 58 extending at an angle thereto. The catching surface 56 extends approximately on a radial line in relation to the spindle 28.

The arresting arrangement 42 has the said three catch noses 48, which are designed as triangular recesses in the edge region 46. The triangular recesses each have a catching surface 60, these surfaces being approximately parallel to the catching surface 56.

The catch tongue 50 and the catch noses 48 are dimensioned in such a way that the catching surface 56 can in each case interact with the catching surface 60 of the three catch noses 48 over as full an area as possible. In order to facilitate release of the catch connection, each catch nose 48 has a surface 62 extending downward to the left at an angle in relation to the catching surface 60. This surface 62 interacts with the surface 58 extending at an angle of the catch tongue 50 in such a way that the catch tongue arrangement 44 is moved out of the catch nose 48 when a downward movement takes place.

In order to ensure that the catch tongue 50 passes into the upper catch nose 48 when the lever arm 26 is moved out of the first end position, the edge region has an upper edge surface 64 falling to the left at an angle (related to the illustration shown in FIG. 2). This edge surface 64 prevents the catch nose 50 passing onto the rear side 66, facing away from the catch noses 48, of the edge region 46 when the lever arm 26 is moved out of the first end position.

An edge surface 68 which (related to the illustration in FIG. 2) falls to the left at an angle is likewise provided at the lower end of the edge region 46. The purpose of this edge surface 68 is to guide the catch nose arrangement 44 onto the rear side 66 after the lowest catch nose 48 has been passed and the actuating force has been released. In this connection, the catching surface 56 of the catch tongue 50 slides along the edge surface 68.

With the aid of this catch mechanism, it is consequently possible to lock the lever arm 26 in three predetermined catching positions and to bring it back into the original, first end position by pressing the lever arm 26 into the lower, second end position 34 and then releasing it. In this connection, the spring force acting on the lever arm 26 causes the catch tongue 50 to slide along the lower edge surface 68 and to be guided onto the rear side 66 of the arresting arrangement 42. As there are no catch noses here, the lever arm 26 can pivot back into the first end position unhindered.

Figure 3:
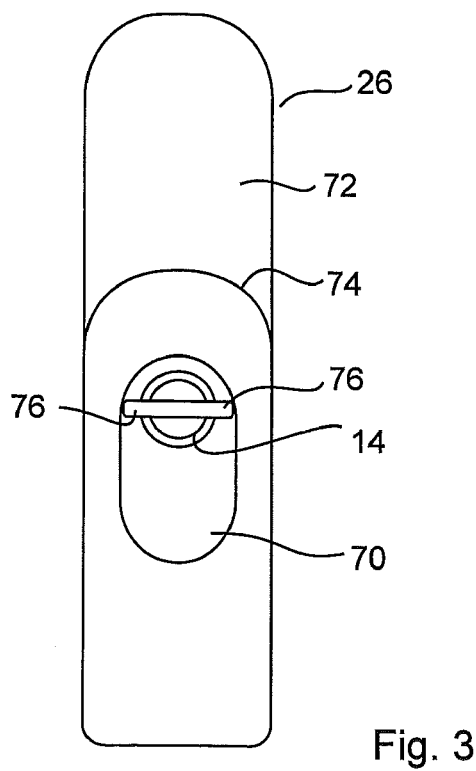
FIG. 3 shows a diagrammatic top view of the lever arm.

FIG. 3 shows the lever arm 26 in an enlarged diagrammatic illustration. In this connection, it can be seen that the lever arm 26 has an elongated hole 70, through which the lateral tube 14 extends. Moreover, the lever arm 26 has a recessed grip 72, which ends at the edge 74 illustrated.

FIG. 3 also shows that the lateral tube 14 has two laterally provided webs 76 which lie in a radial plane (related to the lateral tube 14). The dimension in the radial direction (in relation to the lateral tube 14) is selected in such a way that the webs 76 end shortly before the respective edge of the elongated hole 70. These webs 76 are intended to prevent the lever arm 26 being capable of moving at right angles to the longitudinal axis. This is because such a movement at right angles (parallel to the spindle 28) could result in the catch tongue 50 coming out of a catch nose 48 as catch nose 48 and catch tongue 50 extend in this direction (at right angles to the longitudinal axis of the valve body). The webs 76 consequently serve for guiding the lever arm 26 in a plane of rotation. As emerges from FIG. 1, the webs 76 extend longitudinally in relation to the lateral tube 14 in the direction of the valve body 12.

Figure 4:
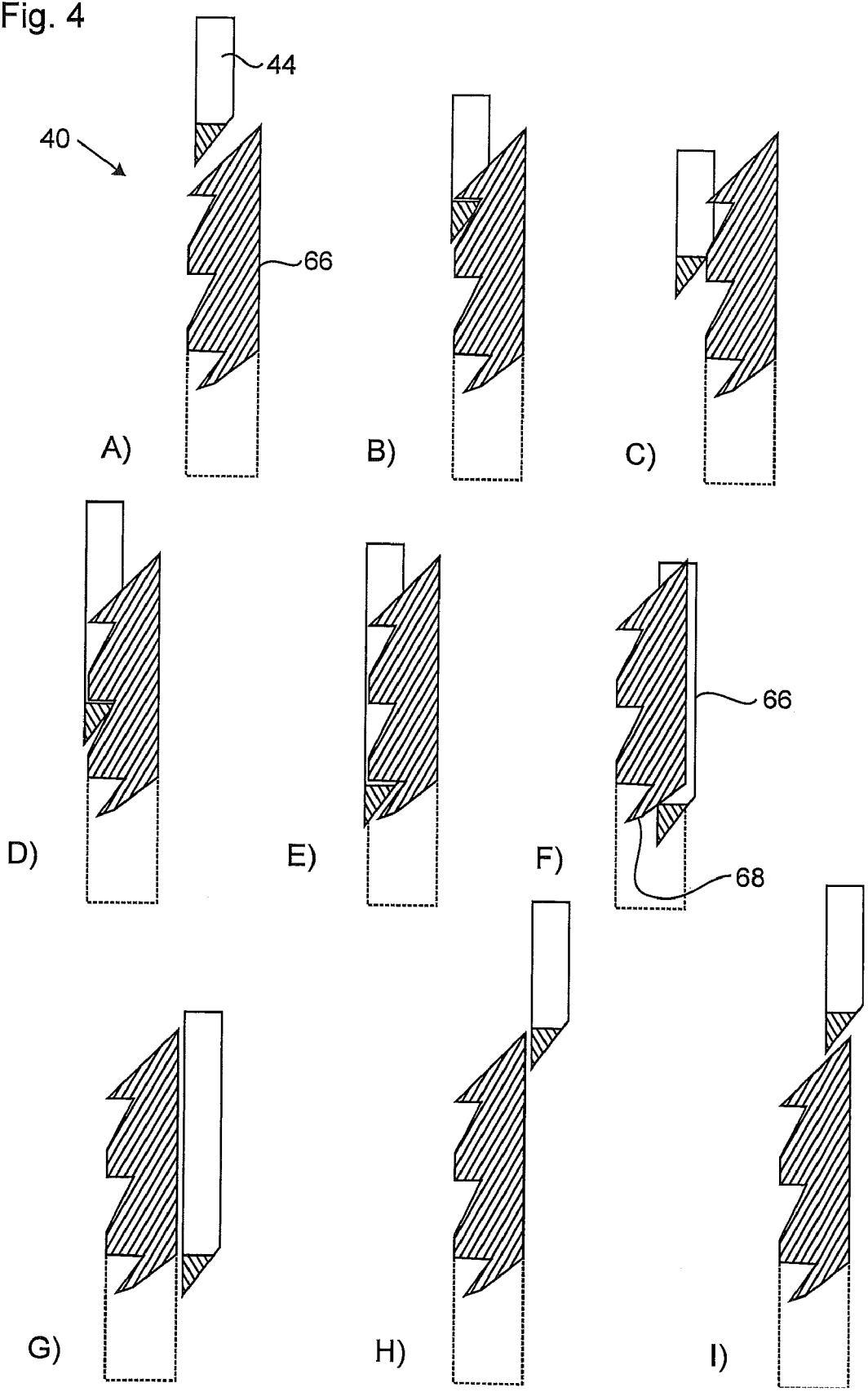
FIGS. 4A to 4I show different illustrations of the catch mechanism in different positions in order to describe its functioning.

The functioning of the catch mechanism 40 is explained again, in detail, in FIGS. 4A to 4I. For simplification, however, the reference numbers used in FIG. 2 have not been shown again. In this connection, the sequence of the positions illustrated in FIGS. 4A to 4I corresponds to a movement of the lever arm 26 from the first, upper end position into the second, lower end position 34 and back into the first end position again. FIG. 4B shows the catch tongue arrangement 44 in a first catching position, FIG. 4D in a second catching position and FIG. 4E in a third catching position. If the lever arm 26 is pressed further in the direction of the valve body 12 counter to the spring force 30, the catch tongue 50 passes onto the edge surface 68, as illustrated in FIG. 4F, and slides along this onto the rear side 66 of the arresting arrangement 42 when the lever arm 26 is released. On this rear side 66, the catch tongue 50 then slides upward back into the first end position, as illustrated in FIGS. 4G to 4I.

As the lever arm 26 and thus the catch tongue 50 cannot be moved in the direction of the spindle. 28, which is prevented by the webs 76, the lever arm 26 can be brought back into the first end position from any of the catching positions only by movement into the second end position 34. It is consequently not possible to move back directly into the first end position from a catching position.

As the user of the device 10 accordingly has to perform only one movement of the lever arm 26 for catching and releasing the lever arm, operation is especially easy.

Therefore, what is claimed, is:

1. A device for handling a catheter comprising:
   a valve body;
   a lever arm which is prestressed by means of a spring element and mounted pivotably on the valve body so as to be pivotable from a first end position into a second end position counter to the prestressing force of the spring element,
   a pressure piston which is received in the valve body and can be moved in a longitudinal direction by means of the lever arm in order to open a sealing element in the valve body when the lever arm is moved in the direction of the second end position, and
   a catch mechanism comprising an arresting arrangement with a front side having a catch nose and a rear side, and a catch tongue interacting with the catch nose in order to hold the lever arm in at least one catching position intermediate said first and second end positions,
   wherein the catch mechanism further comprises a guide surface adapted to guide the catch tongue from the front side to the rear side of said arresting arrangement when the second end position of the lever arm is reached, so that the catch tongue cannot enter into engagement with the catch nose and the spring element guides the lever arm along the rear side back into the first end position.

2. The device according to claim 1, wherein the arresting arrangement has a number of catch noses which are arranged along a concentric line around the fulcrum of the lever arm in order to define a number of catching positions of the lever arm between the first and second end positions.

3. The device according to claim 1, wherein said guide surface extends at an angle from said front side to said rear side of said arresting arrangement.

4. The device according to claim 2, wherein said guide surface extends at an angle from said front side to said rear side of said arresting arrangement.

5. The device according to claim 2, wherein the catch tongue and the catch noses extend transversely to the longitudinal direction of the valve body.

6. The device according to claim 1, wherein the lever arm has an elongated hole, through which a lateral tube starting from the valve body extends.

7. The device according to claim 1, wherein the valve body and the arresting arrangement are designed as a one-piece component.

\* \* \* \* \*